United States Patent [19]

Yurugi et al.

[11] 4,005,201
[45] Jan. 25, 1977

[54] 7-(HYDROXYPHENYL)PYRIDO(3,4-d)PYRIDAZINES

[75] Inventors: Shojiro Yurugi, Kyoto; Shintaro Kikuchi, Hyogo, both of Japan

[73] Assignee: Takeda Chemical Industries, Ltd., Osaka, Japan

[22] Filed: Mar. 25, 1975

[21] Appl. No.: 562,034

[30] Foreign Application Priority Data

Mar. 25, 1974 Japan .............................. 49-33679

[52] U.S. Cl. .......................... 424/248.57; 424/250; 260/246 B; 260/250 AC
[51] Int. Cl.² .............. C07D 405/14; C07D 471/14
[58] Field of Search ................ 260/246 B, 250 AC; 424/248, 250

[56] References Cited
OTHER PUBLICATIONS

Shojiro Yurugi et al., Chemical Abstracts, vol. 78, 43400h (1973).
Shojiro Yurugi et al., Chemical Abstracts, vol. 79, 78,830w (1973).

*Primary Examiner*—Donald G. Daus
*Assistant Examiner*—Jose Tovar
*Attorney, Agent, or Firm*—Wenderoth, Lind & Ponack

[57] ABSTRACT

Novel 7-(hydroxyphenyl)pyrido(3,4-d)pyridazines of the formula:

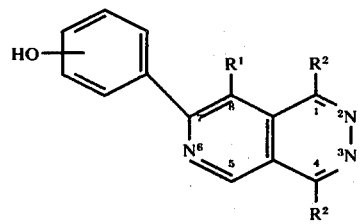

wherein $R^1$ stands for hydrogen or a lower alkyl group; $R^2$ stands for a cyclic amino group, or a pharmaceutically acceptable salt thereof, have excellent diuretic activity in mammals including human beings, so that they are useful for therapy for human or animal use.

10 Claims, No Drawings

7-(HYDROXYPHENYL)PYRIDO(3,4-d)PYRIDAZINES

The present invention relates to novel 7-(hydroxyphenyl)pyrido(3,4-d)pyridazines which have effective diuretic action.

There have been synthesized many kinds of diuretics, and some of them have been applied in practice, typical examples of which are chlorothiazide derivatives, acetazolamide, triamterene, trifrocine, furosemide, etc.

However, known diuretics are not very satisfactory in view of one or more of such disadvantages as promoting the excretion of potassium as well as sodium, causing side effects (e.g. increase of blood glucose level and blood uric acid level) upon long-term administration, and showing rather low diuretic activity and rather high toxicity.

The present inventors have sought to provide an effective diuretic which is unaccompanied by such disadvantages.

Accordingly, the present inventors have synthesized novel 7-(hydroxyphenyl)pyrido(3,4-d)pyridazines and found out that these compounds display excellent diuretic activity and are useful as improved diuretics.

The present invention has been accomplished on the basis of this finding.

Thus, the principal object of the present invention is to provide novel 7-(hydroxyphenyl)pyrido(3,4-d)pyridazines as well as their salts which are useful as effective and improved diuretics. Another object is to provide an industrially feasible method for the production of these novel compounds.

The 7-(hydroxyphenyl)pyrido(3,4-d)pyridazines of the present invention mean compounds represented by the following formula:

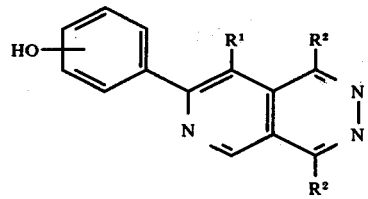

(I)

wherein $R^1$ stands for hydrogen or a lower alkyl group; $R^2$ stands for a cyclic amino group and pharmaceutically acceptable salts thereof.

The lower alkyl group represented by R may for example be methyl, ethyl, propyl, isopropyl or butyl. The cyclic amino group represented by $R^2$ is a five-or six-membered ring containing one or more nitrogen atoms such as, for example, piperidino, pyrrolidino, morpholino, etc., which may have lower alkyl groups having the same meaning as $R^1$. Thus, 2-methylmorpholino, 2,6-dimethylmorpholino, 2,3-dimethylmorpholino, etc. may be mentioned as the example. Furthermore, in pyridazine compounds (I), the substituents at 1- and 4-positions may be different from each other. The pharmaceutically acceptable salts of the compound (I) include the corresponding nontoxic cation salts such as sodium salt, potassium salt or the like. There also are cases in which the compound (I) forms the corresponding inorganic salts such as hydrochloric acid salt, sulfuric acid salt, nitric acid salt, phosphoric acid salt or the like and the corresponding organic acid salts such as oxalic acid salt, fumaric acid salt, tartaric acid salt, malic acid salt, trifluoroacetic acid salt or the like.

The compound of the general formula (I) or its pharmaceutically acceptable salt is prepared by per se known methods, such as the methods described in Dutch Patent Application No. 7217773. A preferable method one of them is the method which comprises reacting a compound of the formula:

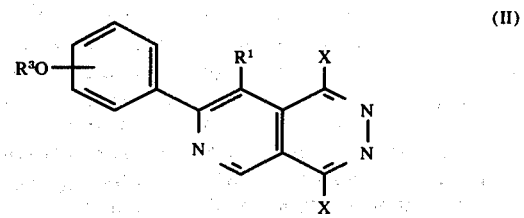

(II)

wherein $R^1$ has the meaning defined above; X stands for halogen; $R^3$ stands for hydrogen, a lower alkyl or aralkyl group, with the cyclic amine corresponding to the cyclic amino group represented by $R_2$ of the compound (I), and, when $R^3$ stands for a lower alkyl or aralkyl group, subjecting thus obtained compound to a reaction leading to cleavage of the ether bond.

The halogen represented by X may for example be chlorine, bromine or iodine. The lower alkyl group represented by $R^3$ may for example be those mentioned in $R^1$, and the aralkyl group represented by $R^3$ may for example be benzyl, phenethyl or the like.

While the reaction of compound (II) with cyclic amine proceeds even in the absence of a solvent, the use of a suitable solvent allows the reaction to proceed more smoothly. The solvent used for this reaction may be any solvent which does not hinder the reaction, and is exemplified by alcohols, e.g. methanol, ethanol, etc.; ethers, e.g. tetrahydrofuran, ethyl ether, etc.; hydrocarbons and halogenated hydrocarbons, e.g. benzene, chloroform, etc.; and esters, e.g. ethyl acetate. As for the amount of cyclic amine, about 2 to 4 moles of the amine to each mole of compound (II) is commonly employed so that it will also function as the reaction solvent and acid acceptor as well. There are no particular limits to the conditions of reaction inclusive of temperature and time. Thus, this reaction proceeds even at room temperature and may be hastened by heating the reaction system to a temperature up to the boiling point of the solvent used or of cyclic amine. Usually, the reaction temperature is in a range from −20° C to 300° C, preferably from 15° C to 150° C. The reaction time is commonly about 1 to 5 hours, although it varies with the particular starting material and solvent used or other factors.

Further, when $R^3$ in the thus obtained compound is a lower alkyl or aralkyl group, thus obtained compound or its reaction mixture in the above method is subjected successively or after isolation to a reaction leading to cleavage of the ether bonds. The procedure used for this ether-cleavage reaction may be any procedure by which the substituent group $R^3O-$ on the 7-phenyl group can be cleaved to a hydroxyl group and, accordingly, it may commonly be hydrolysis or reduction, for instance. When a hydrolytic procedure is employed, it is preferably carried out in water which optionally may be added with an organic solvent and in the presence of a suitable acid. Commonly, the said acid is exemplified by inorganic acids such as hydrochloric acid, hydrobromic acid, hydroiodic acid, etc.; organic acids such as trifluoroacetic acid, toluenesulfonic acid, etc.; and Lewis acids such as aluminum chloride, boron trichloride, boron trifluoride and so on. The organic solvent may be any organic solvent that does not interfere with the reaction, and when the acid is liquid, a large excess of the acid may be used so that it will function as the solvent as well. As for the reaction temperature, the present reaction proceeds well at room temperature but for the purpose of controlling the reaction velocity, it may be conducted under appropriate heating or cooling, depending upon the nature of the acid employed. Commonly, the reaction is carried out in the range of −70° to +130° C. The reductive procedure is particularly advantageous when $R^3$ is an aralkyl group. Any reductive means may be employed insofar as the object can thereby be accomplished, but a particularly advantageous procedure involves catalytic reduction with hydrogen using, as a catalyst, a metal such as palladium, platinum, Raney nickel or the like or a mixture of such a metal and a support material such as, for example, carbon, barium carbonate, calcium carbonate or diatomaceus earth. Usually, this reaction is carried out in water or an organic solvent. While the reaction is commonly carried out at room temperature with success, it may be conducted under cooling or heating in certain cases, the preferred range being from 0° C to 100° C. The pressure of hydrogen may be atmospheric, although a superatmospheric pressure of about 1 to 150 kg./cm² may be employed. The end product of general formula (I) thus obtained can be recovered and purified by conventional procedures such as extraction with a suitable solvent (e.g. water, ethyl acetate, benzene, chloroform, ethanol), recrystallization, column chromatography and so on.

The contemplated compound (I) obtained in the foregoing manner may be put to use with the 7-phenolic hydroxyl group being a free hydroxyl or after it has been converted to the salt of a nontoxic cation such as, sodium or potassium. There also are cases in which the compound (I) forms a salt with an organic acid such as, oxalic acid, fumaric acid, tartaric acid, malic acid or trifluoroacetic acid, or with an inorganic acid such as, hydrochloric acid, sulfuric acid, nitric acid or phosphoric acid. It should be understood that the starting compounds (II) may be used also in the form of salts with such acids.

The starting compound (II) used in the method of this invention can be prepared by per se known methods, e.g. the methods described in Dutch patent application No. 7,217,773, some of these methods are illustrated in the following scheme.

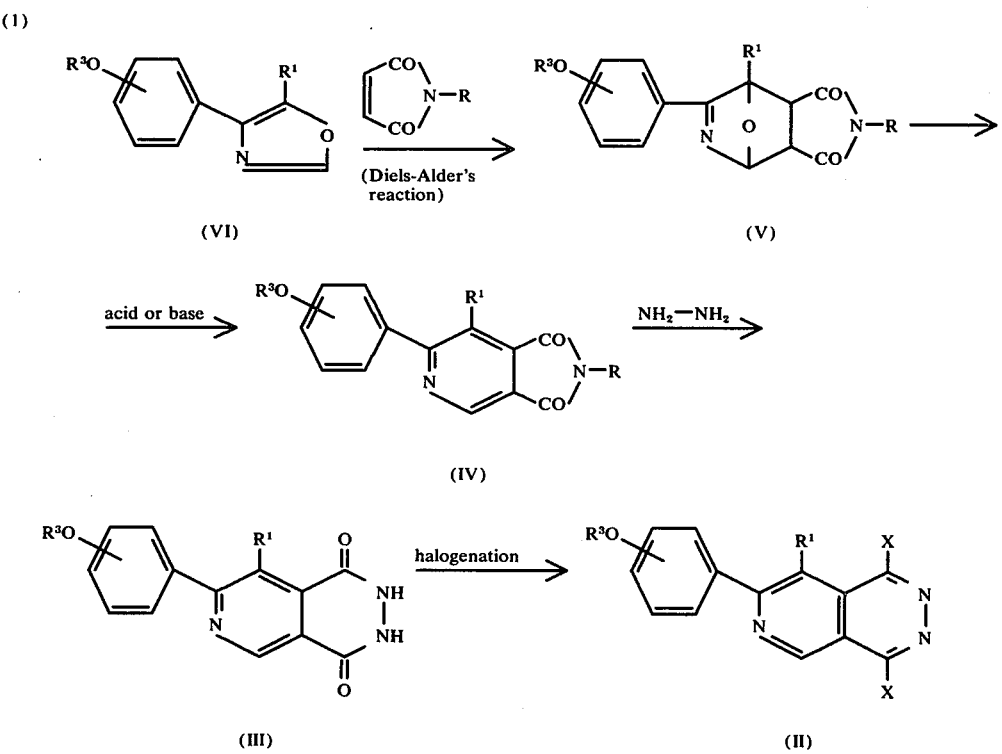

($R^1$, $R^2$, $R^3$ and X have the meaning defined above; R stands for a lower alkyl group)

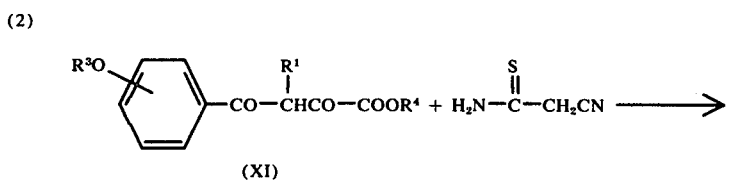

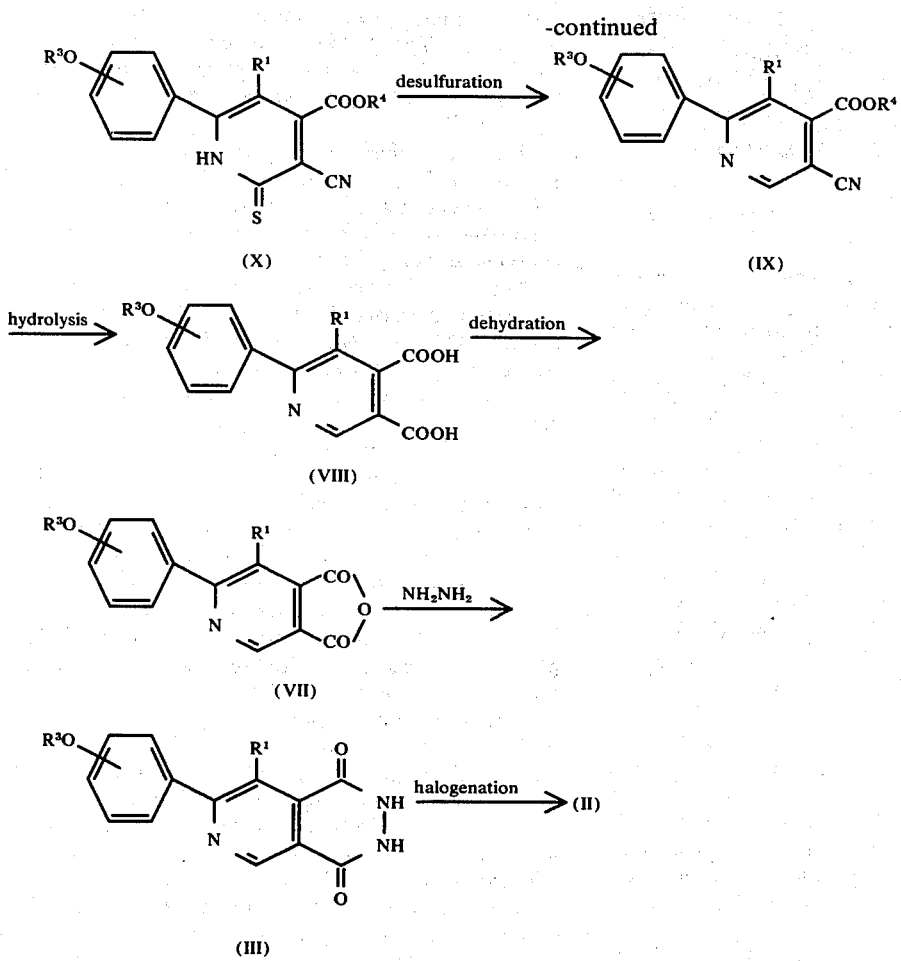

($R^1$ and $R^3$ have the meaning defined hereinbefore; $R^4$ stands for a lower alkyl group)

The contemplated compounds (I) as well as pharmaceutically acceptable salts thereof, which can be produced in the above manner, have excellent diuretic activity in mammals including human beings and are of value as diuretics. In more detail, the present compounds have the following properties:

1. The compounds of this invention have effective and strong diuretic action.
2. They show extremely low toxicity.
3. They are soluble in water.
4. They induce urinary excretion of a large amount of sodium ion, but induce urinary excretion of relatively small amount of potassium ion which is an essential element to the human body. Thus, the excretion ratio of urinary $Na^+/K^+$ is comparatively high in the present compounds.
5. The present compounds can produce a marked additional diuretic response in the animal undergoing maximum diuresis with known diuretics. This fact suggests that the mechanism of diuretic action of the present compounds is different from those of known diuretics. Thus, combination of the present compounds with other known diuretics can produce a much increased diuretic effect.

Therefore, the compounds of the present invention can be used as diuretics for treating ascites including congestive heart failure, liver cirrhosis, hypertension, nephritis, uremia, etc. The purpose of the use may be achieved by using the compound alone, or in the form of a pharmaceutically acceptable composition in admixture with a suitable and conventional carrier or adjuvant. The pharmaceutical composition may take the form of tablets, granules, powders, capsules, injections and may be administered orally or parenterally. Usual daily doses of the compounds lie in the range of about 10 to about 200 milligrams per human adult upon oral administration or of about 5 to 100 milligrams parenteral administration. Some examples of practical formulations in which compound (I) of this invention is utilized as remedies for congestive heart failure, liver cirrhosis, hypertension or nephritis, are as follows:

| | | |
|---|---|---|
| (1) | 7-(4-hydroxyphenyl)-1,4-dimorpholinopyrido-(3,4-d)pyridazine | 50 mg. |
| | | 50 mg./capsule |
| (2) | 7-(4-hydroxyphenyl)-1,4-dimorpholinopyrido-(3,4-d)pyridazine | 50 mg. |
| | lactose | 50 mg. |
| | | 100 mg./capsule |
| (3) | 7-(4-hydroxyphenyl)-8-methyl-1,4-dimorpholino-pyrido(3,4-d)pyridazine | 50 mg. |
| | corn starch | 50 mg. |
| | | 100 mg./capsule |

It is to be understood that the following examples are solely for the purpose of illustration and not to be construed as limitations of this invention, and that many variations may be restored to without departing from the spirit and scope of this invention. In this specification, "g.", "kg.", "ml.", "l.", "decomp." and "calcd.", are "gram", "kilogram", "milliliter", "liter", "decomposed" and "calculated", respectively.

The preparation of the starting compound (II)

1.

1,4-dichloro-7-(4-hydroxyphenyl)-pyrido(3,4-d)-pyridazine

A mixture of 35 g. of 4-hydroxyphenacyl bromide, 150 ml. of formamide and 120 ml. of glacial acetic acid was heated at 120°–130° C for 6.5 hours and the acetic acid was distilled off under reduced pressure.

The residue was poured in 300 ml. of ice-water and extracted four times with ethyl acetate. The extract was dried over anhydrous sodium sulfate and the ethyl acetate was distilled off, whereupon 4-(4-hydroxyphenyl) oxazole is obtained. To this product was added 30 g. of N-phenyl-maleinimide and the mixture was heated on an oil bath at 120°–130° C for 4 hours. After cooling, ethanol was added and the resultant crystals were recovered by filtration. The described procedure yielded 25 g. of 2-(4-hydroxyphenyl)-N-phenylpyridine-4,5-dicarboximide melting at 250°–260° C (decomp.).

Elemental analysis, for $C_{19}H_{12}O_3N_2$. Calcd: C, 72,14; H, 3,82; N, 8.86; Found: C, 71.82; H, 3.71; N, 8.40.

A mixture of 4 g of 2-(4-hydroxyphenyl)-N-phenyl-pyridine-4,5-dicarboximide, 30 ml. of glacial acetic acid and 4 g. of hydrazine hydrate was boiled under reflux for 1 hour and, after cooling, the resultant crystals were recovered by filtration. The procedure yielded 3.2 g. of 7-(4-hydroxyphenyl)-1,2,3,4-tetrahydropyrido(3,4-d)pyridazine-1,4-dione melting at 300° C or up.

Elemental analysis, for $C_{13}H_9O_3N_3$. Calcd: C, 61.17; H, 3.55; N, 16.47; Found: C, 60.48; H, 3.29; N, 16.27.

0.5 g. of 7-(4-hydroxyphenyl)-1,2,3,4-tetrahydropyrido(3,4-d)pyridazine-1,4-dione was heated together with 0.5 ml of α-picoline and 5 ml. of phosphorus oxychloride at 90°–100° C for 3 hours, after which time the reaction mixture was concentrated under reduced pressure. To the residue was added 10 ml. of water and the resultant 0.4 g. of 1,4-dichloro-7-(4-hydroxyphenyl)-pyrido(3,4-d)pyridazine was recovered by filtration. This crude product as such was used in the next reaction.

2.

7-(4-benzyloxyphenyl)-1,4-dichloropyrido(3,4-d)-pyridazine

A mixture of 16 g. of ethyl (4-benzyloxy)benzoyl-pyruvate, 6.7 g. of cyanothioacetamide, 1 ml. of triethylamine and 50 ml. of ethanol was refluxed on a water bath for 2 hours. After cooling, the resultant red-colored crystals were recovered by filtration and washed with ethanol. The above procedure yielded 14 g. of 6-(4-benzyloxyphenyl)-3-cyano-4-ethoxycarbonyl-2(1H)-thiopyridone melting at 155°–160° C.

Elemental analysis, for $C_{22}H_{18}O_3N_2S$. Calcd: C, 67.67; H, 4.65; N, 7.18; Found: C, 67.44; H, 4.53; N, 7.17.

A mixture of 60 g. of 6-(4-benzyloxyphenyl)-3-cyano-4-ethoxycarboxyl-2(1H)-thiopyridone and 1.2 kg. of Raney nickel in 1.2 l. of acetone was stirred under reflux for 1 hour. The Raney nickel was filtered off and the filtrate was concentrated and, then, chromatographed on a column packed with silica gel, followed by elution with a mixed solvent of benzene-acetone (4:1). The combined eluate is concentrated to yield 16 g. of 6-(4-benzyloxyphenyl)-3-cyano-4-ethoxycarbonyl pyridine as colorless needles melting at 135°–137° C.

Elemental analysis, for $C_{22}H_{18}O_3N_2$; Calcd: C, 73.73; H, 5.06; N, 7.82. Found: C, 73.81; H, 5.01; N, 7.63;

In a sealed tube, 9 g. of 6-(4-benzyloxyphenyl)-3-cyano-4-ethoxycarbonylpyridine and 180 ml. of 10% aqueous sodium hydroxide solution were heated at 150°–160° c for 3 hours, after which the reaction mixture was concentrated. The concentrate was rendered acidic with concentrated hydrochloric acid and the resultant crystals were recovered by filtration, dried and recrystallized from acetic acid. The procedure yielded 8.7 g. of 6-(4-benzyloxyphenyl)-cinchomeronic acid as pale-yellow flakes melting at 253°–255° C.

Elemental analysis, for $C_{20}H_{14}O_5N$. Calcd: C, 68,76; H, 4.33; N, 4.01; Found: C, 68.30; H, 4.29; N, 3.84.

A mixture of 8.0 g. of 6-(4-benzyloxyphenyl)cinchomeronic acid and 160 ml. of acetic anhydride was refluxed for 1 hour, after which the insolubles were filtered off when the solution was warm. The filtrate was then cooled, whereupon 4.7 g. of 6-(4-benzyloxyphenyl)cinchomeronic anhydride was obtained as yellow crystals melting at 216°–°C.

Elemental analysis, for $C_{20}H_{12}O_4N$. Calcd: C, 72.50; H, 3.96; N, 4.23; Found: C, 72.75; H, 3.94; N, 3.99.

A mixed solution of 6.5 g. of 6-(4-benzyloxyphenyl)-cinchomeronic anhydride and 13 ml. of hydrazine hydrate in 65 ml. of acetic acid was stirred under reflux for 2 hours. After cooling, water was added to the reaction mixture and the resultant crystals were recovered by filtration, washed with water and dried. The procedure yielded 6.0 g. of 7-(4-benzyloxyphenyl)-1,4-dioxo-1,2,3,4-tetrahydropyrido(3,4-d)pyridazine as colorless crystals melting at 300° C or up.

Elemental analysis, for $C_{20}H_{15}O_3N_3$. Calcd: C, 69.55; H, 4.38; N, 12.17; Found: C, 69.27; H, 4.16; N, 11.83.

A mixture of 10 g. of 7-(4-benzyloxyphenyl)-1,4-dioxo-1,2,3,4-tetrahydropyrido(3,4-d)pyridazine, 100 ml. of phosphorus oxychloride and 10 ml. of phosphorus oxychloride and 10 ml of α-picoline was stirred at 100°–110° C for 3 hours. The reaction mixture was concentrated under reduced pressure and the residue was decomposed with ice-water. The resultant crystals were recovered by filtration, washed with water and dried to give 11.0 g. of objective compound.

EXAMPLE 1

To 0.4 g. of the 1,4-dichloro-7-(4-hydroxyphenyl)-pyrido(3,4-d)pyridazine was added 10 g. of morpholine and the mixture was heated at 130° C for 4 hours. The morpholine was then distilled off and 10 ml. of water was added to the residue. The insolubles were recovered by filtration and then, the filtrate was chromatographed on a column packed with silica gel, followed by elution with benzene-acetone (4:1). The combined eluate is concentrated to yield 0.1 g. of 7-(4-hydroxyphenyl)-1,4-dimorpholinopyrido(3,4-d)pyridazine melting at 285°–287° C.

Elemental analysis, for $C_{21}H_{23}O_3N_5$. Calcd: C, 64.11; H, 5.89; N, 17.80; Found: C, 63.97; H, 5.84; N, 17.90.

EXAMPLE 2

1. 11.0 g. of 7-(4-benzyloxyphenyl)-1,4-dichloropyrido-(3,4-d)pyridazine was then reacted with 50 ml. of morpholine under reflux for 4 hours. The reaction mixture was concentrated under reduced pressure and water was added to the residue. The resultant crystals were recovered by filtration, washed with water, dried and recrystallized from a solvent mixture of ethyl acetate and ethanol. The procedure yielded 8.5 g. of 7-(4-benzyloxyphenyl)-1,4-dimorpholinopyrido(3,4-d)pyridazine as yellow crystals melting at 206°–208° C.

Elemental analysis, for $C_{28}H_{29}O_3N_5$. Calcd: C, 69.54; H, 6.05; N, 14.48; Found: C, 69.54; H, 6.09; N, 13.94.

2. A solution of 7.0 g. of 7-(4-benzyloxyphenyl)-1,4-dimoropholinopyrido(3,4-d)pyridazine in 70 ml. of trifluoroacetic acid was stirred under reflux for 0.5 hour, after which time the reaction mixture was concentrated under reduced pressure. To the residue was added 50 ml. of benzene, followed by reconcentration.

The residue was dissolved in 20 ml. of methanol and a saturated aqueous solution of sodium hydrogen carbonate was added. The resultant yellow crystals were recovered by filtration, washed with water, dried and recrystallized from a mixture of ethyl acetate and methanol. The procedure yielded 4.7 g. of 7-(4-hydroxyphenyl)-1,4-dimorpholinopyrido(3,4-d)pyridazine as pale yellow needles melting at 285°–287° C.

Elemental analysis, for $C_{21}H_{23}O_3N_5$. Calcd: C, 64.11; H, 5.89; N, 17.80; Found: C, 63.98; H, 5.74; N, 17.94.

EXAMPLE 3

In 20 ml. of ethanol was dissolved 1 g. of 7-(4-benzyloxyphenyl)-1,4-dimorpholinopyrido(3,4-d)pyridazine and, after the addition of 0.1 g. of palladium-on-carbon (10%), the solution was stirred in hydrogen gas streams and at room temperature for 5 hours. The catalyst was filtered off and the filtrate was concentrated. The residue was then recrystallized from a mixture of ethyl acetate and methanol. The procedure yielded 0.5 g. of 7-(4-hydroxyphenyl)-1,4-dimorpholinopyrido(3,4-d)pyridazine melting at 285°–287° C. Mixture-melting with a sample according to Example 1 showed no depression in melting point.

EXAMPLE 4

1. In a procedure similar to (1) in Example 2, 1.3 g. of 7-(4-methoxyphenyl)-1,4-dichloropyrido(3,4-d)pyridazine is used instead of 7-(4-benzyloxyphenyl)-1,4-dichloropyrido-(3,4-d)pyridazine, whereby 1.0 g. of 7-(4-methoxyphenyl-1,4-dimorpholinopyrido is obtained.

2. In 10 ml. of methylene chloride was dissolved in 1 g. of 7-(4-methoxyphenyl)-1,4-dimorpholinopyrido(3,4-d)pyridazine obtained in (1) and the solution was cooled to −40° C. Meanwhile, 1 g. of boron tribromide was dissolved in methylene chloride to prepare 1 M solution and this solution was gradually added to the first-mentioned solution with stirring. After 5 hours, the solvent was distilled off under reduced pressure and the residue was heated together with ethanol under reflux for 1 hour. The reaction solvent was distilled off and the residue was recrystallized from a mixture of ethyl acetate and methanol. The procedure yielded 0.5 g. of 7-(4-hydroxyphenyl)-1,4-dimorpholinopyrido(3,4-d)pyridazine melting at 285°–287° C. Mixture-melting with a sample according to Example 1 showed no depression in melting point.

EXAMPLE 5

1. In a procedure similar to (1) in Example 2, 2.5 g. of 7-(4-isopropyloxyphenyl)-1,4-dichloropyrido(3,4-d)pyridazine is used instead of 7-(4-benzyloxyphenyl)-1,4-dichloropyrido-(3,4-d)pyridazine, whereby 2.0 g. of 7-(4-isopropyloxyphenyl)-1,4-dimorpholinopyrido(3,4-d)pyridazine is obtained.

2. To a mixture of 20 ml. of glacial acetic acid and 6 ml. of 47% aqueous hydrogen bromide solution was added 2 g. of 7-(4-isopropyloxyphenyl)-1,4-dimorpholinopyrido(3,4-d)-pyridazine obtained in (1) and, after the mixture was boiled under reflux for 2 hours, it was concentrated to dryness under reduced pressure. The residue was dissolved in 5 ml. of methanol and the solution was neutralized with saturated sodium carbonate solution. Following the addition of 20 ml. of water, the solution was extracted with chloroform. The solvent was distilled off from the extract and the residue was purified by column chromatography on silica gel (developer solvent; benzene:acetone=1:1) in the same manner described in Example 1. The procedure yielded 0.3 g. of 7-(4-hydroxyphenyl)-1,4-dimorpholinopyrido(3,4-d)pyridazine melting at 285°–287° C. Mixture-melting with a sample according to Example 1 showed no melting point depression.

EXAMPLE 6

1. In a procedure similar to (1) in Example 2, 80 g. of 2-methylmorpholine instead of morpholine is reacted with 1.7 g of 7-(4-benzyloxyphenyl)-1,4-dichloropyrido(3,4-d)-pyridazine, whereby 1.3 g. of 7-(4-benzyloxyphenyl)-1,4-bis-(2-methylmorpholino)-pyrido(3,4-d)pyridazine is obtained.

2. A solution of 1.3 g. of 7-(4-benzyloxyphenyl)-1,4-bis-(2-methylmorpholino)-pyrido(3,4-d)pyridazine obtained in (1) in 13 ml. of trifluoroacetic acid was stirred under reflux for 0.5 hour and the reaction mixture was then concentrated under reduced pressure. To the residue was added 10 ml. of benzene, followed by reconcentration. The residue was dissolved in 5 ml. of methanol and, then, a saturated aqueous solution of sodium hydrogen carbonate was added. The resultant yellow crystals were recovered by filtration, washed with water, dried and recrystallized from a mixture of ethyl acetate and methanol. The procedure yielded 0.6 g. of 7-(4-hydroxyphenyl)-1,4-bis-(2-methylmorpholino)-pyrido-(3,4-d)pyridazine as yellow needles melting at 266°–268° C.

Elemental analysis, for $C_{23}H_{27}O_3N_5 \cdot \frac{1}{2}H_2O$. Calcd: C, 64.63; H, 6.56; N, 16.27; Found: C, 65.11; H, 6.33; N, 16.11.

EXAMPLE 7

1. In a procedure similar to (1) in Example 2, 7.0 g. of piperidine instead of morpholine is reacted with 1.7 g. of 7-(4-benzyloxyphenyl)-1,4-dichloropyrido(3,4-d)pyridazine, whereby 1.2 g. of 7-(4-benzyloxyphenyl)-1,4-dipiperidinopyrido(3,4-d)pyridazine is obtained.

2. A solution of 1.2 g. of 7-(4-benzyloxyphenyl)-1,4-dipiperidinopyrido(3,4-d)pyridazine obtained in (1) in 12 ml. of trifluoroacetic acid was stirred under reflux for 0.5 hour, at the end of which time the reaction mixture was concentrated under reduced pressure. To the residue was added 10 ml. of benzene, followed by reconcentration. The residue was dissolved in 5 ml. of methanol and a saturated aqueous solution of sodium hydrogen carbonate was then added. The resultant yellow crystals were recovered by filtration, washed with water, dried and recrystallized from a mixture of ethyl acetate and ethanol. The procedure yielded 0.6 g.

of 7-(4-hydroxyphenyl)-1,4-dipiperidinopyrido[3,4-d]-pyridazine.

Elemental analysis, for $C_{23}H_{27}ON_5 \cdot \frac{1}{2}H_2O$. Calcd: C, 69.82; H, 7.08; N, 17.57; Found: C, 70.52; H, 6.96; N, 17.18.

EXAMPLE 8

1. In a procedure similar to (1) in Example 2, 2.6 g. of 7-(4-benzyloxyphenyl)-8-methyl-1,4-dichloropyrido(3,4-d)-pyridazine is used instead of 7-(4-benzyloxyphenyl)-1,4-dichloropyrido(3,4-d)pyridazine, whereby 2.0 g. of 7-(4-benzyloxyphenyl)-8-methyl-1,4-dimorpholinopyrido(3,4-d)-pyridazine is obtained.

2. A solution of 2.0 g. of 7-(4-benzyloxyphenyl)-8-methyl-1,4-dimorpholinopyrido(3,4-d)pyridazine obtained in (1) in 20 ml. of trifluoroacetic acid was refluxed for 40 minutes, after which the trifluoroacetic acid was distilled off under reduced pressure. To the residue was added 20 ml. of benzene, followed by concentration to dryness. The residue was neutralized with a saturated aqueous solution of sodium hydrogen carbonate and extracted with chloroform. The extract was dried over anhydrous sodium sulfate and the chloroform was distilled off. Recrystallization of the crude crystalline residue from ethanol yielded 1.2 g. of 7-(4-hydroxyphenyl)-8-methyl-1,4-dimorpholinopyrido(3,4-d)-pyridazine as yellow needles melting at 264°–266° C.

Elemental analysis, for $C_{22}H_{25}O_3N_5$. Calcd: C, 64.85; H, 6.18; N, 17.19; Found: C, 64,74; H, 6.14; N, 17.05.

EXAMPLE 9

1. In a procedure similar to (1) in Example 2, 2.5 g. of 7-(3-benzyloxyphenyl)-1,4-dichloropyrido(3,4-d)pyridazine is used instead of 7-(4-benzyloxyphenyl)-1,4-dichloropyrido-(3,4-d)pyridazine, whereby 2.0 g. of 7-(3-benzyloxyphenyl)-1,4-dimorpholinopyrido(3,4-d)pyridazine is obtained.

2. A solution of 2.0 g. of 7-(3-benzyloxyphenyl)-1,4-dimorpholinopyrido(3,4-d)pyridazine obtained from (1) in 20 ml. of trifluoroacetic acid was stirred under reflux for 0.5 hour. The reaction mixture was concentrated under reduced pressure and 10 ml. of benzene was added to the residue, followed by reconcentration. The residue was dissolved in 5 ml. of methanol and a saturated aqueous solution of sodium hydrogen carbonate was added. The resultant yellow crystals were recovered by filtration, washed with water, dried and finally recrystallized from ethyl acetate. The procedure yielded 1.3 g. of 7-(3-hydroxyphenyl)-1,4-dimorpholinopyrido(3,4-d)pyridazine trifluoroacetate as yellow needlets melting at 277°–279° C.

Elemental analysis, for $C_{21}H_{23}O_3N_5 \cdot CF_3COOH$. Calcd: C, 61.73; H, 5.41; N, 15.65; Found: C, 61.54; H, 5.46; N, 15.71.

EXAMPLE 10

1. In a procedure similar to (1) in Example 2, 3.7 g. of 7-(2-benzyloxyphenyl)-1,4-dichloropyrido(3,4-d)pyridazine is used instead of 7-(4-benzyloxyphenyl)-1,4-dichloropyrido-(3,4-d)pyridazine, whereby 3.0 g. of 7-(2-benzyloxyphenyl)-1,4-dimorpholinopyrido(3,4-d)pyridazine is obtained.

2. A solution of 3.0 g. of 7-(2-benzyloxyphenyl)-1,4-dimorpholinopyrido(3,4-d)pyridazine obtained in (1) in 30 ml. of trifluoroacetic acid was stirred under reflux for 0.5 hour. The reaction mixture was concentrated under reduced pressure and 20 ml. of benzene was added to the residue, followed by reconcentration. The residue was dissolved in 10 ml. of methanol and a saturated aqueous solution of sodium hydrogen carbonate was added. The resultant yellow crystals were recovered by filtration, washed with water, dried and finally recrystallized from ethyl acetate. The procedure yielded 2.0 g. of 7-(2-hydroxyphenyl)-1,4-dimorpholinopyrido(3,4-d)pyridazine as yellow powders melting at 250°–253° C.

Elemental analysis, for $C_{21}H_{23}O_3N_5$. Calcd: C, 64.11; H, 5.89; N, 17.80; Found: C, 64.21; H, 5.99; N, 17.31.

What is claimed is:

1. A pyrido [3,4-d] pyridazine shown by the formula:

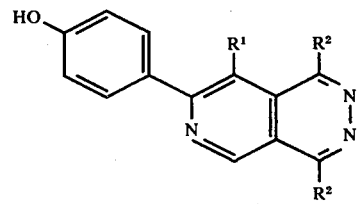

wherein $R^1$ stands for hydrogen or methyl, $R^2$ stands for morpholino, methyl-morpholino, ethyl-morpholino, piperidino, methyl-piperidino or ethyl-piperidino or a pharmaceutically acceptable nontoxic cation salt or a pharmaceutically acceptable nontoxic acid addition salt thereof.

2. A pyrido [3,4-d] pyridazine as claimed in claim 1 wherein $R^2$ is morpholino, methyl-morpholino or ethyl-morpholino.

3. A pyrido(3,4-d)pyridazine as claimed in claim 1, wherein $R^2$ is morpholino.

4. The pyrido(3,4-d)pyridazine as claimed in claim 3, which is 7-(4-hydroxyphenyl)-1,4-dimorpholinopyrido(3,4-d)pyridazine.

5. The pyrido(3,4-d)pyridazine as claimed in claim 3, which is 7-(4-hydroxyphenyl)-8-methyl-1,4-dimorpholinopyrido(3,4-d)pyridazine.

6. A pyrido [3,4-d] pyridazine as claimed in claim 1, wherein $R^2$ is methyl-morpholino or ethyl-morpholino.

7. The pyrido(3,4-d)pyridazine as claimed in claim 6 which is 7-(4-hydroxyphenyl)-1,4-bis-(2-methyl-morpholino)-pyrido(3,4-d)pyridazine.

8. A pyrido [3,4-d]pyridazine as claimed in claim 1 wherein $R^2$ is piperidino, methyl-piperidino or ethyl-piperidino.

9. The pyrido(3,4-d)pyridazine as claimed in claim 8 which is 7-(4-hydroxyphenyl)-1,4-dipiperidinopyrido(3,4-d)pyridazine.

10. A method of treating ascites consisting essentially of administering a medicinally effective amount of a compound of claim 1.

* * * * *